United States Patent [19]
Guarracino et al.

[11] Patent Number: 6,080,908
[45] Date of Patent: *Jun. 27, 2000

[54] ODOR CONTROL MATERIAL

[75] Inventors: Mario Guarracino, Silivi; Giovanni Carlucci, Chieti, both of Italy

[73] Assignees: Centro Ricerche Fater P & G S.p.A., Sambuceto, Italy; The Procter & Gamble Company, Cincinnati, Ohio

[ * ] Notice: This patent is subject to a terminal disclaimer.

[21] Appl. No.: 09/213,940

[22] Filed: Dec. 17, 1998

Related U.S. Application Data

[63] Continuation of application No. 08/537,887, Jan. 22, 1996, Pat. No. 5,944,704.

[30] Foreign Application Priority Data

Apr. 23, 1993 [IT] Italy .................................. TO93A0278

[51] Int. Cl.⁷ ...................................................... A61F 13/15
[52] U.S. Cl. ........................................... 604/359; 604/360
[58] Field of Search ...................................... 604/359, 358, 604/360

[56] References Cited

U.S. PATENT DOCUMENTS

| | | | |
|---|---|---|---|
| 4,263,873 | 4/1981 | Christianson | 119/1 |
| 4,949,672 | 8/1990 | Ratcliff et al. | 119/1 |
| 5,407,442 | 4/1995 | Karapasha | 604/359 |

FOREIGN PATENT DOCUMENTS

| | | | |
|---|---|---|---|
| 510619 A1 | 10/1992 | European Pat. Off. | 604/359 |
| J6 1179155 | 8/1986 | Japan | 604/359 |
| 004 823 | 2/1988 | Japan | 604/359 |

*Primary Examiner*—Mark O. Polutta
*Attorney, Agent, or Firm*—Darby & Darby

[57] ABSTRACT

An absorbent article for absorbing bodily fluid, incorporating a buffer having a pH of from 7 to 10 acting as an efficient odor control material for preventing or combating malodorous compounds present in such articles in use.

3 Claims, 1 Drawing Sheet

ODOR CONTROL MATERIAL

CROSS-REFERENCED TO THE RELATED APPLICATIONS

This is a continuation of Application No. 08/537,887, filed Jan. 22, 1996, U.S. Pat. No. 5,944,704 which was the National Stage of International Application No. PCT/EP94/01263, filed Apr. 22, 1994, and claims priority to Italian Application TO93A000278, filed Apr. 23, 1993.

STATEMENT REGARDING FEDERALLY SPONSORED RESEARCH OR DEVELOPMENT

Not applicable

BACKGROUND OF THE INVENTION

1. Field of the Invention

This invention relates to an absorbent article comprising a odour control material and in particular to an article for absorbing fluids, for example, bodily fluids, the said article comprising an odour control material which is a buffer.

Absorbent articles are designed to be worn by humans to absorb bodily fluids, such as urine, menstrual fluid and perspiration, etc. Examples of absorbent articles include sanitary napkins, pantiliners, disposable diapers, incontinence pads, tampons and the like.

2. Description of the Related Art Including Information Disclosed Under 37 C.F.R. 1.97 and 1.98.

In use, the absorbent articles are known to acquire a variety of compounds, for example volatile fatty acids (e.g. isovaleric acid), ammonia, amines (e.g. triethylamine), fatty acids, sulphur containing compounds (e.g. mercaptans, sulphides), alcohols, ketones and aldehydes (e.g. furaldehyde) which release unpleasant odours. These compounds may be present in the bodily fluid or may be produced by fermentation once the bodily fluid is absorbed into the pad. In addition menstrual fluid which contains microorganisms can also generate malodorous by products. Unpleasant odours which emanate from absorbent pads when in use may make the wearer feel self conscious.

A number of compounds, mixtures, compositions and the like are known to combat some of the unpleasant odours referred to above many of which are based on absorbents such as activated carbon, clay and zeolites.

U.S. Pat. No. 3,939,838 discloses an article for treating menstrual fluid having the function of effectively removing odour that is released from menstrual fluid. The odour controls exemplified are active carbon, active silica, active alumina, ion exchange resin and chlorophyll.

EP-A-0509409 discloses an absorbent article which contains an anhydrous non-buffer odour control mixture which includes at least basic and pH neutral odour absorbing particles, and optionally acidic odour absorbing particles. It is disclosed that for feminine articles very small amounts of acid, less than about 10%, preferably less than about 5% and most preferably less than about 1% of the total weight of the deodorizing mixture is required. The basic odour absorbing particle can be used between about 25 to 99%, preferably 75 to 95%, of the total deodorizing mixture and the pH neutral odour absorbing particles may be included in about 1 to 25 and preferably 15 to 20% of the total weight of the deodorizing mixture.

U.S. Pat. No. 3,995,636 discloses a catamenial device, in particular a tampon, which comprises a segment of a rapidly re-expandable hydrophilic polymeric foam held in compression by a constraining means. The constraining means comprises a coating material that includes a mixture of citric acid and sodium bicarbonate. It is disclosed that the coating composition restores the slightly acidic environment in the vaginal area and thus prevents undue accumulation of noxious odour and irritation which results from enzymic reduction of uric acid, urea, amino acids and the like constituting menstrual discharge, to ammonia and volatile amines.

U.S. Pat. No. 5,122,407 discloses an absorbent pad cover having lasting odour control effect and in particular discloses a non-woven web of fibrous material, a fluorocarbon polymer composition adhered to the fibres throughout the web, an odour absorbing reagent bound to the web by the fluorocarbon composition and rendered hydrophoric thereby and a plurality of apertures defined through the web. Suggested odour absorbing reagents are activated carbon, ABSCENTS (ABSCENTS is a registered Trade Mark) (synthetic zeolite), sodium bicarbonate and carbonates, bicarbonates, phosphates, biphosphates, sulfates and bisulphates of alkali and alkaline earth metals; ascorbic acid, boric acid, citric acid and maleic acid.

U.S. Pat. No. 5,130,352 discloses mouldable filled polyethylene compositions containing particulate lignocellulosic fillers. Boric acid and/or borax is added to the composition to suppress odour during manufacture and processing of the compositions.

Some previously used absorbents are not particularly efficient in removing unpleasant odours. Other absorbents, whilst efficient at removing unpleasant odours, may have other disadvantages and, for example, the black colour of carbon black is aesthetically unappealing in an absorbent pad.

BRIEF SUMMARY OF THE INVENTION

The object of the present invention is to provide an absorbent article, for example, for absorbing bodily fluids, having incorporated therein an odour control material which is efficient in preventing or combating malodorous compounds present in such articles in use and which is not subject to the aesthetic disadvantages referred to above.

It has been surprisingly found that materials which act as buffers and have a pH of from 7 to 10, act as very efficient odour control materials.

Accordingly as a first aspect the present invention provides an absorbent article, for example, for absorbing bodily fluids, having incorporated therein a buffer, as odour control material, which buffer has a pH of from 7 to 10. Preferably the pH of the buffer is from 8 to 9.

To measure the pH of the buffer, hereinafter called an odour control material, 100 ml of a 1% (weight) solution of the odour control material is prepared by dissolving, at room temperature with continued stirring, the odour control material in distilled water. The pH may be measured with a Metrohm 670 Titro processor and a Metrohm Combined pH Glass Electrode, which has been previously calibrated with two buffer solutions at pH 7 and pH 4.

According to a second aspect, the present invention provides an absorbent article having incorporated therein an odour control material which comprises a salt of the formula $[X^+]_2[B_4O_7]^{2-}$ or $[X^{2+}][B_4O_7]^{2-}$ wherein $X^+$ is Na, K, or Li and $X^{2+}$ is Ca or Mg, and an acid wherein the acid is boric acid, citric acid, tartaric acid or ascorbic acid.

The salt may be present in hydrous (e.g. decahydrate) or anhydrous form. The acid is preferably boric acid.

Particularly preferably the odour control material comprises boric acid and sodium tetraborate.

The ratio in % by weight of the acid to the salt which may be used in the odour control material is preferably 80:20 to 10:90, more preferably 75:25 to 15:85, particularly preferably 60:40 to 40:60. Most preferably the ratio is about 50:50.

The absorbent article may be a sanitary napkin, a pantiliner, a disposable diaper, an incontinence pad, a tampon or the like. According to one aspect of the invention the absorbent article is a pantiliner.

The weight of the odour control material which may be used in the absorbent article can be readily determined by the skilled person bearing in mind the size of the absorbent article in question. For example a suitable quantity of odour control material which may be used in a pantiliner is from 0.15 g to 2.0 g, preferably the quantity is from 0.5 g to 1.0 g.

Optionally, other conventional compounds may be included in the article together with the odour control material, for example one or more of the following may be incorporated, activated carbon, zeolite absorbents, charcoal, anti-microbial agents, ionic absorbants such as an absorbent gelling material (AGM) or known odour control materials. The quantity of those compounds which may be added can be readily determined by those skilled in the art.

Preferably AGM, is included in the article together with the odour control material of the present invention. The quantity of AGM which may be added may be readily determined by those skilled in the art for each absorbent article. Preferably 0–0.7 g and more preferably 0–0.5 g of AGM is added to a pantiliner. If the quantity of AGM exceeds 0.7 g the effectiveness of the odour control material decreases.

More preferably AGM, zeolite and activated carbon are included in the article together with the odour control material of the present invention.

The odour control material may be incorporated into the article by methods disclosed in the art, for example layered on the core of the absorbent material or mixed within the fibers of the absorbent core. The odour control material is preferably incorporated between two layers of cellulose tissue, optionally the material may be bonded between two cellulose tissue layers with, for example, a hot melt adhesive or any suitable bonding system.

The odour control material may be used in any of its forms. Preferably it is in powder form.

The odour control material of the present invention has surprisingly been found to prevent and combat the release of malodorous compounds, as referred to above, in absorbent articles by means of a buffering mechanism. The odour control material has also been found to inhibit growth of microorganisms that are responsible for the release of unpleasant odours.

It has also surprisingly been found that the odour control material of the present invention works more efficiently than a previously known buffering system, namely the citric acid, sodium bicarbonate odour control system.

Additional advantages of the invention are that the acids and salts used as the odour control material, and in particular the boric acid and sodium tetraborate, are white powders and are thus aesthetically appealing. In addition they are safe and relatively low cost materials.

BRIEF DESCRIPTION OF THE SEVERAL VIEWS OF THE DRAWING

The invention will now be illustrated with reference to the detailed description and examples taken in conjunction with the accompanying Figures.

DETAILED DESCRIPTION OF THE INVENTION

Figure 1:
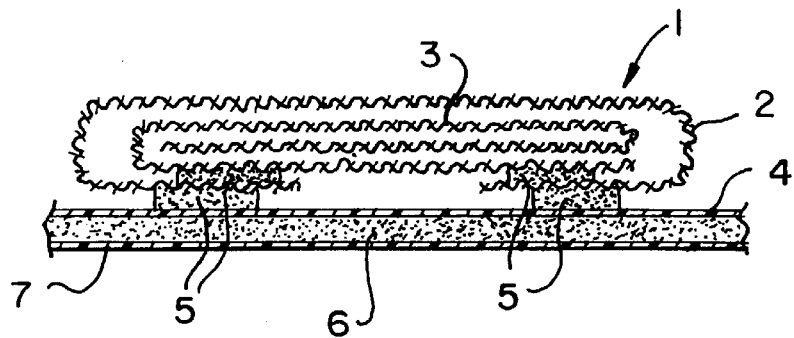
FIG. 1 shows a cross sectional view of a commercially available Always® pantiliner Always is a registered trademark.
Figure 2:
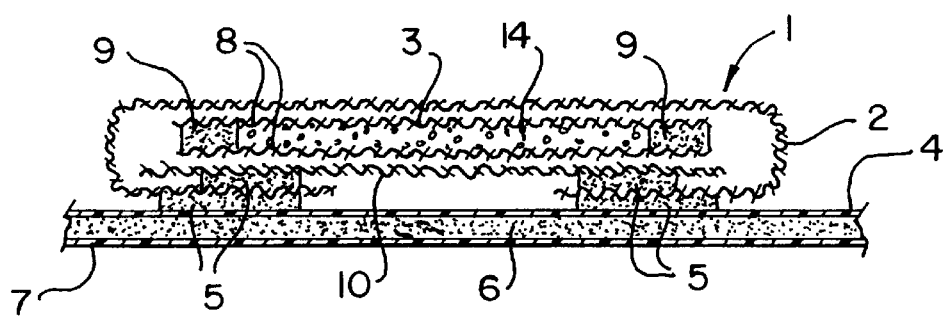
FIG. 2 shows a cross sectional view of a pantiliner having an absorbent core comprising three cellulose tissue layers, the odour control material being incorporated between the first and second tissue layers.
Figure 3:
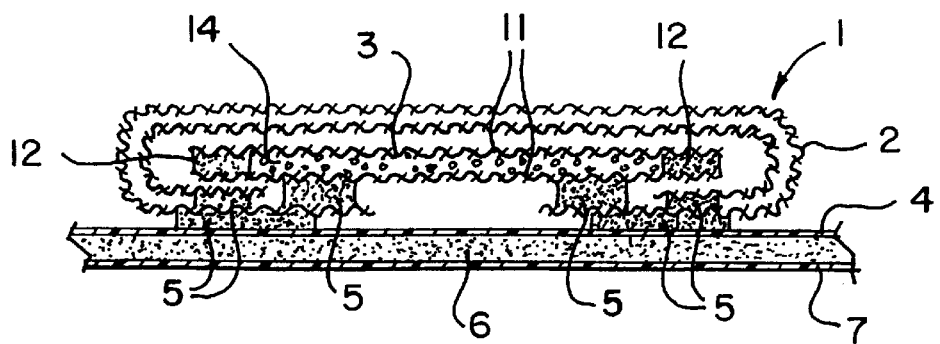
FIG. 3 shows a cross sectional view of a pantiliner having an absorbent core comprising three cellulose tissue layers, the odour control material being incorporated between the second and third tissue layers.

An absorbent article, namely a pantiliner which is an exemplary embodiment of an article into which the odour control material of the present invention may be incorporated, is shown in cross section in FIGS. 1 to 3.

The pantiliner may be of any shape known in the art, for example, rectangular, hour glass, winged, etc.

As shown in FIGS. 1 to 3 pantiliner 1 comprises a liquid pervious topsheet 2, an absorbent core 3, a liquid impervious backsheet 4, adhesive 5 which fastens the topsheet 2 to the backsheet 4 and the absorbent core 3 to topsheet 2, a layer of adhesive 6 which is secured to the backsheet 4 and which is covered by removable release liner 7. It is not, however, intended that the pantiliner should be limited to embodiments comprising all such elements. Additional elements known to the skilled person may also be included in the pantiliner.

Topsheet 2 is liquid permeable and, when pantiliner 1 is in use, is in close proximity to the skin of the user. Topsheet 2 is compliant, soft feeling and non-irritating to the user's skin. It can be made from any of the conventional materials for this type of use. Nonlimiting examples of suitable materials that can be utilized as the topsheet 2 are woven and nonwoven polyester, polypropylene, nylon and rayon and formed thermoplastic films, with formed films being preferred. Suitable formed films are described in U.S. Pat. No. 4,324,246, U.S. Pat. No. 4,324,214, U.S. Pat. No. 4,341,217 and U.S. Pat. No. 4,463,045.

The formed films are preferred for topsheet 2 because they are pervious to liquids and yet non-absorbent. Thus, the surface of the formed film, which is in contact with the body, remains dry and is more comfortable to the wearer. The topsheet may be constituted by the covering structure for sanitary products described in EP-A-0 207 904. Preferably the topsheet 2 is made of polyethylene perforated film (24.5 g/m$^2$)

The outer surface of topsheet 2 may be treated with a surfactant. Treating the outer surface of topsheet 2 with surfactant renders such surface more hydrophilic which results in liquid penetrating topsheet 2 faster than if the surface were not treated. It is preferred that the surfactant be substantially evenly and completely distributed throughout the outer surface of topsheet 2. This can be accomplished by any of the common techniques well known to those skilled in the art. For example, the surfactant can be applied to topsheet 2 by spraying, by padding or by the use of transfer rolls.

The inner surface of topsheet 2 nay be secured in contacting relation to absorbent core 3. This contacting relationship results in liquid penetrating the topsheet 2 faster than if it were not in contact with absorbent core 3. Topsheet 2 can be maintained in contact with the absorbent core 3 by applying adhesive, preferably in spaced limited areas, to the inner surface of the topsheet 2. Examples of suitable adhesives used for such purpose include the acrylic emulsion E-1833BT manufactured by the Rohm & Haas Company, Philadelphia, Pa. and the acrylic emulsion WB 3805 manufactured by H.B. Fuller Company of St. Paul, Minn. The adhesives can be applied by the same methods as the surfactant is applied to the outer surface of the topsheet 2.

Preferably the topsheet 2 wraps around the core 3, as shown in FIGS. 1 to 3, and is fastened by means of an adhesive 5 to backsheet 4.

Referring again to FIGS. 1 to 3, it can be seen that absorbent core 3 is positioned between topsheet 1 and backsheet 4. Absorbent core 3 provides the absorptive means for absorbing the bodily fluid. Absorbent core 3 is generally compressible, conformable and non-irritating to the user's skin. It can comprise any material used in the art for such purpose. Examples of such materials include multiple plies of creped cellulose wadding, fluffed cellulose fibers, wood pulp fibers also known as airfelt, textile fibers, a blend of fibers, a mass or batt of fibers, a web of polymeric fibers, a blend of polyester and polypropylene fibers, layers of cellulose tissue or layers of air laid tissue.

Preferably, the core comprises a mass or batt of fibers. While many types of fibers may be used, a preferred material is a batt of polyester fibers. More preferably the core comprises cellulose tissue (40.61 g/m$^2$) which forms three absorbent layers. FIG. 1 shows an absorbent core 3 formed by one layer of cellulose tissue which has been folded as shown to form three absorbent layers. FIG. 2 shows an absorbent core comprised of two layers of air laid cellulose tissue 8 joined at their longitudinal edges with adhesive 9 and having a layer of cellulose tissue 10 therebeneath to form the three layered absorbent core. FIG. 3 shows two layers of air laid tissue 11 joined at their longitudinal edges with adhesive 12 and having a layer of cellulose tissue 13 wrapped therearound to for, the third layer of the absorbent core.

Preferably, the odour control material disclosed herewith is incorporated into the absorbent core by known techniques. It may, for example, be layered on the absorbent core or mixed with the fibers of the core. More preferably the odour control material 14 is placed between two layers of air laid cellulose tissue as shown in FIGS. 2 and 3 above.

Referring to FIGS. 1 to 3, the pantiliner is provided with a backsheet 4 which backsheet is impervious to liquids and, thus, prevents menstrual fluid which may be expressed from absorbent core 3 for soiling the body or clothing of the user. Suitable materials are well known in the art, including woven and nonwoven fabrics which have been treated to render them liquid repellent. Breathable or vapor pervious, liquid resistant materials, and those materials described in U.S. Pat. No. 3,881,489 and U.S. Pat. No. 3,989,86 can also be used. Preferred materials are those materials that are fluid and vapor impervious, because they provide additional fluid strikethough protection. Especially preferred materials include formed thermoplastic films. One especially suitable material is a polyethylene film having a thickness of from about 0.075 mils to about 1.25 mils, with a 1.0 mil thickness polyethylene film being especially suitable. Preferably the backsheet 4 is polyethylene embossed film (24.4 g/m$^2$)

The outer surface of backsheet 4 is coated with adhesive 6. Adhesive 6 provides a means for securing the pantiliner in the crotch portion of a panty. Any adhesive or glue used in the art for such purpose can be used herein, with pressure sensitive adhesives being preferred. Suitable adhesives are Century A-305-IV manufactured by the Century Adhesives Corporation and Instant Lok 34-2823 manufactured by the National Starch and Chemical Corporation. Also, before pantiliner 1 is placed in use, the pressure sensitive adhesive 6 should be covered with removable release liner 7 in order to keep adhesive 6 from drying out or sticking to a surface other than the crotch portion of the panty prior to use. Any commercially available release liners commonly used for such purposes can be utilized herein. Nonlimiting examples of suitable release liners are BL 30 MG-A Silox E1/O and BL 30 MG-A Silox 4 P/O both of which are manufactured by the Akrosil Corporation. Preferably the release liner is a silicon paper having a thickness of about 45 μm (43.5 g/m$^2$). Other means which are known in the art may be used to affix the pantiliner in the crotch portion of a panty.

The invention will now be illustrated with reference to the examples wherein the article for absorbing bodily fluids is a pantiliner or a sanitary napkin and the odour control material is boric acid and sodium tetraborate. It will, of course, be appreciated that other absorbent articles may also have the odour control material incorporated therein, the incorporation of the odour control material into the pantiliner may be achieved by other known methods and the odour control material may be any of those disclosed in the present specification.

EXAMPLES

Incorporation of the Odour Control Material into a Pantiliner

The pantiliners used in the following examples were Always pantiliners (Always is a Registered Trade Mark) as sold by the Procter & Gamble Company. Each pantiliner was opened by cutting the polyethylene (PE) perforated film along a longitudinal edge of the product at its bottom face. The upper two layers of the inner three-folded cellulose tissue sheet, which constitutes the absorbent core of the product, were cut away and substituted with two layers of cellulose air laid tissue. The odour control material in the form of a powder was homogeneously dispersed between said two layers. The whole pantiliner structure was then reconstituted and sealed along the edges by means of adhesive. FIG. 2 represents a sectional view of the pantiliner structure which comprises a topsheet 2, airlaid layers 8 joined at their longitudinal edges with adhesive lines 9, the odour control material 14, a tissue layer 10, a backsheet 4, an adhesive layer 6 and a removable release liner 7.

Ten different samples were prepared by the method as described above, which samples incorporate various combinations of odour control material (OCM), namely boric acid and sodium tetraborate in powder form, and, optionally, other compounds like absorbent gelling materials (AGM) and/or zeolites with activated carbon (ZC), as illustrated in Table 1 below wherein the quantity of odour control material, in grams, incorporated in each sample is shown.

The AGM used in the samples is a polyacrylate from The Dow Chemical Company known by the name of Drytech 2090, the zeolite and activated carbon are as disclosed in WO 91/12030.

A commercially available Always (Always is a Registered Trade Mark) pantiliner without modification was used as a reference (Blank Sample 0).

TABLE 1

| Sample | Quantity of material in g | | |
|---|---|---|---|
| | OCM | AGM | ZC |
| 1 | 0.90 | — | — |
| 2 | 0.90 | 0.10 | — |
| 3 | 0.60 | 0.30 | — |
| 4 | 0.90 | 0.45 | — |
| 5 | 0.60 | 0.10 | 0.30 |
| 6 | — | 0.30 | 0.30 |
| 7 | 0.80 | 0.20 | — |
| 8 | 0.80[a] | 0.20 | — |
| 9 | 0.80[b] | 0.20 | — |
| 10 | 0.80[c] | 0.20 | — |
| 0 | — | — | — |

[a] Boric acid 0.16 g+Na tetraborate 0.64 g
[b] Boric acid 0.08 g+Na tetraborate 0.72 g
[c] Boric acid 0.64 g+Na tetraborate 0.16 g Unless stated otherwise, the ratio by weight of the components of the OCM is 50/50 boric acid/sodium tetraborate; the ratio by weight of the components of the ZC is approximately 50/50 zeolite/activated carbon.

Odour Control Test Protocol

Each test comprises four separate stages which may be summarised as follows:
a) consignment of the products.
b) Product return and preparation of the test samples.
c) Sniff-test.
d) Statistical analysis of the Data.

Each stage is described in more detail below.
a) Women were chosen who were known to have an odour control problem. Each of five women selected were given one product per test sample individually packaged in an anonymous bag. Every product was worn for seven hours.
b) The used product was placed into an aluminum tray, approximately 1 cm deep, covered with a perforated aluminum sheet, in order to keep it out of view, and finally covered with another tray of the same type, which was kept thereon in inverted position up to the moment of the sniff-test.
c) The sniff-test was performed in a "pre-ventilated" room by five graders Each grader had been preselected for their sensitivity to the unpleasant smells present in an absorbent article after use and their ability to grade the unpleasantness of the odour in a consistent manner. Every grader evaluated the odour of each series of five products representing each sample using a pleasantness scale which ranges from -10 (highest level of unpleasantness) to 5 (most pleasant), passing though 0 (neutral rating). The pleasantness values for each sample were obtained as a mean of 25 observations (five graders, five products for each sample).
d) The results collected from the test were then analysed by statistical analysis software (SAS). The data was processed in order to show statistically significant differences between the treated and untreated products.

This difference is shown in the tables by means of a letter (in the "Significant difference" column) near every mean value; results with the same letter are not statistically significantly different.

The student's two-tailed "t" test was used to compare the data between two types of samples (see example 1), while Duncan's Multiple Range test was used to perform multiple comparisons (see examples 2, 3 and 4).

Values of $p<0.05$ were considered statistically significant.

Example 1

Sample type 1 and a reference blank sample 0 were tested in order to show the odour removing capability of the odour control material of the present invention.

The pleasantness grade values show statistically significant differences between the product with the odour control material and the reference (blank sample 0)

TABLE 2

| Sample type | Significant difference | Mean |
|---|---|---|
| 1 | A | -1.40 |
| 0 | B | -3.13 |

($p < 0.05$)

Example 2

Sample types 2, 3 and 4 with various amounts of AGM and OCM were tested together with the reference (blank sample 0).

It can be seen from the results that all treated samples are statistically different from the reference and in particular all samples having the odour control material of the present invention control the odour when compared to the reference.

TABLE 3

| Sample type | Significant difference | Mean |
|---|---|---|
| 2 | A | -0.92 |
| 3 | B | -1.72 |
| 4 | B | -2.08 |
| 0 | C | -3.13 |

Example 3

The samples tested are type 5, 6 and the reference (blank sample 0). It can be seen that the addition of the OCM has a positive effect on a known system based on a zeolite combined with activated carbon.

TABLE 4

| Sample type | Significant difference | Mean |
|---|---|---|
| 5 | A | -0.64 |
| 6 | B | -1.36 |
| 0 | C | -2.72 |

Example 4

In this test different weight ratios of the two components of the OCM were used; samples 7, 8, 9, 10 and 0 were tested The best results have been achieved with a 50/50 weight ratio between boric acid and sodium tetraborate (Sample 7). The results of samples 8, 9 and 10 were found not to be significantly different and nor were the results for samples 9, 10 and 0. For every weight ratio of the two components the odour control material of the present invention still controls odour when compared to the reference.

TABLE 5

| Sample type | Significant difference | Mean |
|---|---|---|
| 7 | A | -1.35 |
| 8 | B | -2.25 |

TABLE 5-continued

| Sample type | Significant difference | | Mean |
|---|---|---|---|
| 9 | B | C | −2.60 |
| 10 | B | C | −2.60 |
| 0 | | C | −3.16 |

Incorporation of the OCM into a Sanitary Napkin

The samples were obtained from commercially available Lines Liberty Idea sanitary napkins as sold by Fater SpA.

Each napkin is opened by cutting the wrap around perforated coverstock at its bottom face approximately along a longitudinal edge of the release paper which covers the external adhesive layer.

The side of the absorbent fibrous core is then exposed by slightly shifting the water impermeable plastic bottom layer and, subsequently, the fibrous core is split into two halves, each having approximately the same thickness, along a plane which is parallel to the plane of the napkin itself.

The odour control material is homogeneously dispersed between these two fibrous layers which are then joined together to reconstitute the absorbent core.

The water impermeable inner backsheet is then put back into its original position and the wrap around perforated coverstock is sealed along the cut by means of e.g. a double sided adhesive tape.

The test protocol is substantially the same as previously described for the pantiliners, with the exception that the mean values of the unpleasantness obtained from the 25 observations for each sample have been corrected with a statistical technique called "covariance analysis" to take into account the fact that there was not a fixed wearing time for the sanitary napkins.

Example 5

Two treated samples were tested (1S and 2S), together with a reference blank sample (0S).

The OCM's in the treated samples were;

1S: sodium tetraborate 0.7 g/boric acid 0.7 g pH 8.3.
2S: sodium bicarbonate 0.7 g/citric acid 0.7 g (comparative example) pH 5.7.

TABLE 6

| Sample type | Significant difference | Mean |
|---|---|---|
| 1S | A | −2.07 |
| 2S | B | −3.34 |
| 0S | B | −3.63 |

Pleasantness value for sample 1S shows a statistically significant difference from the 2S sample and the blank sample 0S thus indicating a large improvement in odour control.

What is claimed is:

1. An absorbent article having incorporated therein a buffer as odour control material, said buffer comprising an acid and a salt and having a pH of from 7 to 10.

2. An absorbent article as claimed in claim 1 wherein the buffer has a pH of from 8 to 9.

3. A method of controlling odours in an absorbent article by incorporating therein a buffer comprising an acid and a salt and having a pH of from 7 to 10.

* * * * *